US011957310B2

(12) United States Patent
Bagley et al.

(10) Patent No.: US 11,957,310 B2
(45) Date of Patent: Apr. 16, 2024

(54) MEDICAL SYSTEMS, DEVICES, AND RELATED METHODS

(71) Applicant: Boston Scientific Scimed, Inc., Maple Grove, MN (US)

(72) Inventors: Kevin L. Bagley, Natick, MA (US); Serena Scott, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 394 days.

(21) Appl. No.: 17/095,825

(22) Filed: Nov. 12, 2020

(65) Prior Publication Data

US 2021/0145263 A1 May 20, 2021

Related U.S. Application Data

(60) Provisional application No. 62/937,388, filed on Nov. 19, 2019.

(51) Int. Cl.
| | |
|---|---|
| *A61B 1/00* | (2006.01) |
| *A61B 1/005* | (2006.01) |
| *A61B 1/018* | (2006.01) |
| *A61B 1/04* | (2006.01) |

(52) U.S. Cl.
CPC ........ *A61B 1/0014* (2013.01); *A61B 1/00006* (2013.01); *A61B 1/00066* (2013.01); *A61B 1/00121* (2013.01); *A61B 1/00147* (2013.01); *A61B 1/0057* (2013.01); *A61B 1/018* (2013.01); *A61B 1/042* (2013.01); *A61B 1/005* (2013.01)

(58) Field of Classification Search
CPC .............. A61B 1/0014; A61B 1/00006; A61B 1/00066; A61B 1/00121; A61B 1/00147; A61B 1/0057; A61B 1/018; A61B 1/042; A61B 1/005; A61B 1/00; A61B 1/0125; A61B 1/0058; A61B 1/00119; A61M 25/0147
USPC .......................................... 600/114, 104, 153
See application file for complete search history.

(56) References Cited

U.S. PATENT DOCUMENTS

| | | | | |
|---|---|---|---|---|
| 4,245,624 | A * | 1/1981 | Komiya | A61B 1/12 604/95.04 |
| 5,025,778 | A * | 6/1991 | Silverstein | A61B 1/00078 600/117 |
| 5,575,751 | A * | 11/1996 | Walther | A61N 5/0601 600/128 |
| 6,126,649 | A * | 10/2000 | VanTassel | A61M 25/0147 604/95.04 |
| 7,833,156 | B2 * | 11/2010 | Williams | A61B 17/3403 600/184 |
| 7,976,458 | B2 * | 7/2011 | Stefanchik | A61B 1/00154 600/114 |

(Continued)

*Primary Examiner* — Timothy J Neal
*Assistant Examiner* — James Edward Boice
(74) *Attorney, Agent, or Firm* — Bookoff McAndrews, PLLC

(57) ABSTRACT

A medical system includes a plurality of tubes configured to be arranged about a periphery of an insertion device. A lumen of each of the plurality of tubes is configured to receive a medical device. Each of the tubes is configured to be coupled to the periphery of the insertion device and is moveable from a collapsed configuration adjacent the periphery of the insertion device to an expanded configuration further radially outward of the periphery of the insertion device as compared to the collapsed configuration.

20 Claims, 4 Drawing Sheets

(56) References Cited

U.S. PATENT DOCUMENTS

| | | | |
|---|---|---|---|
| 9,358,363 B2 | 6/2016 | Boulais | |
| 2005/0234294 A1* | 10/2005 | Saadat | A61B 1/0008 600/104 |
| 2006/0069304 A1* | 3/2006 | Takemoto | A61B 1/00087 600/104 |
| 2008/0294003 A1* | 11/2008 | Honda | A61B 1/018 600/114 |
| 2009/0259141 A1* | 10/2009 | Ewers | A61B 1/018 600/106 |
| 2010/0036198 A1* | 2/2010 | Tacchino | A61B 17/29 600/106 |
| 2013/0110089 A1* | 5/2013 | Kappel | A61B 1/00098 606/1 |
| 2018/0264239 A1 | 9/2018 | Piskun | |
| 2018/0317899 A1* | 11/2018 | Zada | A61B 1/00135 |

\* cited by examiner

MEDICAL SYSTEMS, DEVICES, AND RELATED METHODS

CROSS-REFERENCE TO RELATED APPLICATIONS

This patent application claims the benefit under 35 U.S.C. § 119 to U.S. Provisional Patent Application No. 62/937,388, filed on Nov. 19, 2019, the entirety of which is incorporated herein by reference

TECHNICAL FIELD

Various aspects of the present disclosure generally relate to medical systems, devices, and related methods that employ multiple medical tools or devices. In particular, aspects of the present disclosure relate to medical systems, devices, and methods for performing a medical procedure using, in some embodiments, medical tools or devices controlled via a robotic control system.

BACKGROUND

Medical devices, such as endoscopes or other suitable insertion devices, are employed for a variety of types of diagnostic and surgical procedures, such as endoscopy, arthroscopy, gynoscopy, thoracoscopy, cystoscopy, etc. Many of these procedures involve delivering an insertion device to a position within the body of a patient. Additionally, many procedures involve delivering a medical device through a lumen in the insertion device. In particular, such procedures may be carried out by inserting the insertion device (e.g., a duodenoscope) into a subject's body through a surgical incision, or via a natural anatomical orifice (e.g., mouth, vagina, or rectum), and performing the procedure or operation at a target site with an auxiliary medical device (e.g., a catheter or other therapeutic or diagnostic tool) inserted through the insertion device.

One challenge in the field of minimally invasive procedures, such as an endoscopy procedure and surgical procedures, is associated with triangulation of medical tools relative to an image capture device. Medical tools are often advanced through a patient's body from the same direction, and any illumination and/or visualization devices used during the procedure often point in this same direction. For example, during an endoscopy procedure, an insertion device is generally inserted into a patient's body, and one or more medical devices are generally inserted through the insertion device to a treatment site within the patient's body. In this aspect, the insertion device and the one or more medical devices are pointing in the same direction, and relative movement between the insertion device and the one or more medical devices may be limited by the insertion of the medical devices through the insertion device. In this scenario, it may be difficult for a user to effectively and/or efficiently manipulate (e.g., extend, rotate, angle, direct, etc.) the insertion device and the one or more medical devices during the procedure. Additionally, the user may be required to hold and/or manipulate the insertion device with one hand, and hold and/or manipulate one or more medical devices with another hand. Alternatively, additional medical professionals may be required to assist the user with holding and/or manipulating the insertion device and the one or more medical devices. These concerns may increase the duration, costs, and risks of the medical procedure.

The systems, devices, and methods of the current disclosure may rectify some of the deficiencies described above or address other aspects of the art.

SUMMARY

Examples of the present disclosure relate to, among other things, systems, devices, and methods for performing one or more medical procedures with the medical systems and devices. Each of the examples disclosed herein may include one or more of the features described in connection with any of the other disclosed examples.

In one example, a medical system may include a plurality of tubes configured to be arranged about a periphery of an insertion device. A lumen of each of the plurality of tubes may be configured to receive a medical device. Each of the tubes may be configured to be coupled to the periphery of the insertion device and may be moveable from a collapsed configuration adjacent the periphery of the insertion device to an expanded configuration further radially outward of the periphery of the insertion device as compared to the collapsed configuration.

The medical system may include one or more of the following features. The medical system may include the insertion device. Each of the plurality of tubes may be coupled to a distal portion of the insertion device via one or more supports that may be movable relative to the insertion device. The one or more supports may bias the tubes toward the expanded configuration. In the expanded configuration, a distal portion of at least one tube may be curved or bent radially inward toward a longitudinal axis of the insertion device. The medical system may further include one or more control wires configured to transition the tubes between the collapsed configuration and the expanded configuration. In the expanded configuration, proximal portions of the tubes may contact the insertion device.

The medical system may further include a control system. The control system may include an adaptor and a controller, and the adaptor may be configured to receive a portion of the medical device. The adaptor may include a base and a slider that is movable relative to the base, and the slider may include a receiving portion configured to receive the portion of the medical device. The controller may be coupled to the adaptor, and the controller may automatically control the movement of the slider relative to the base. The controller may be coupled to the insertion device to automatically control one or more operations of the insertion device. The adaptor may include a plurality of actuators, a plurality of motors, and a plurality of rotatable members coupled to the motors. Each actuator may be configured to be coupled to a handle of a corresponding medical device. The motors and rotatable members may be configured to rotate and/or translate the medical device when the medical device is coupled to the corresponding actuator. The adaptor may include a coupling mechanism with a base and a slider that is movable relative to the base. The base may include a base knob configured to be coupled to a main body of a handle of the medical device, and the slider may include at least one slider knob configured to be coupled a movable body of the handle of the medical device.

The plurality of tubes may include two to six tubes, and the tubes may be approximately evenly spaced around the periphery of the insertion device. The insertion device may include a visualization device positioned at a distal end of the insertion device.

In another aspect, a medical system may include a platform device, an adaptor, and a controller. The platform device may include an inner tube and a plurality of outer tubes arranged about a periphery of the inner tube. Each of the outer tubes may be coupled to a distal portion of the inner tube via one or more supports so that a distal portion of each outer tube can move radially away from a longitudinal axis of the inner tube. Each of the outer tubes may be configured to receive a medical device. The adaptor may be configured to receive a portion of the medical device, the controller may be configured to automatically control movement of the medical device relative to a corresponding outer tube of the plurality of outer tubes.

The medical system may include one or more of the following features. In a configuration in which the distal portion of at least one outer tube is radially away from the longitudinal axis of the inner tube, the distal portion of the at least one outer tube may be curved or bent radially inward toward the longitudinal axis of the inner tube, and a proximal portion of the at least one outer tube may contact the inner tube. The adaptor may include at least one actuator configured to be coupled to a handle of the medical device, a motor, and a rotatable member coupled to the motor. The controller may be coupled to the adaptor and may control the movement of the actuator, the motor, and the rotatable member.

In yet another aspect, a method may include positioning a platform device at a treatment site, where the platform device may include an inner tube and plurality of outer tubes arranged about a periphery of the inner tube, delivering one or more medical devices to the treatment site through one or more of the outer tubes, transitioning one or more of the outer tubes to an expanded configuration in which a distal portion of the one or more outer tubes is further radially away from the periphery of the inner tube, and extending or actuating the one or more of the medical devices.

The method may further include repositioning, replacing, removing, or manipulating the platform device or the one or more medical devices.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Figure 1:
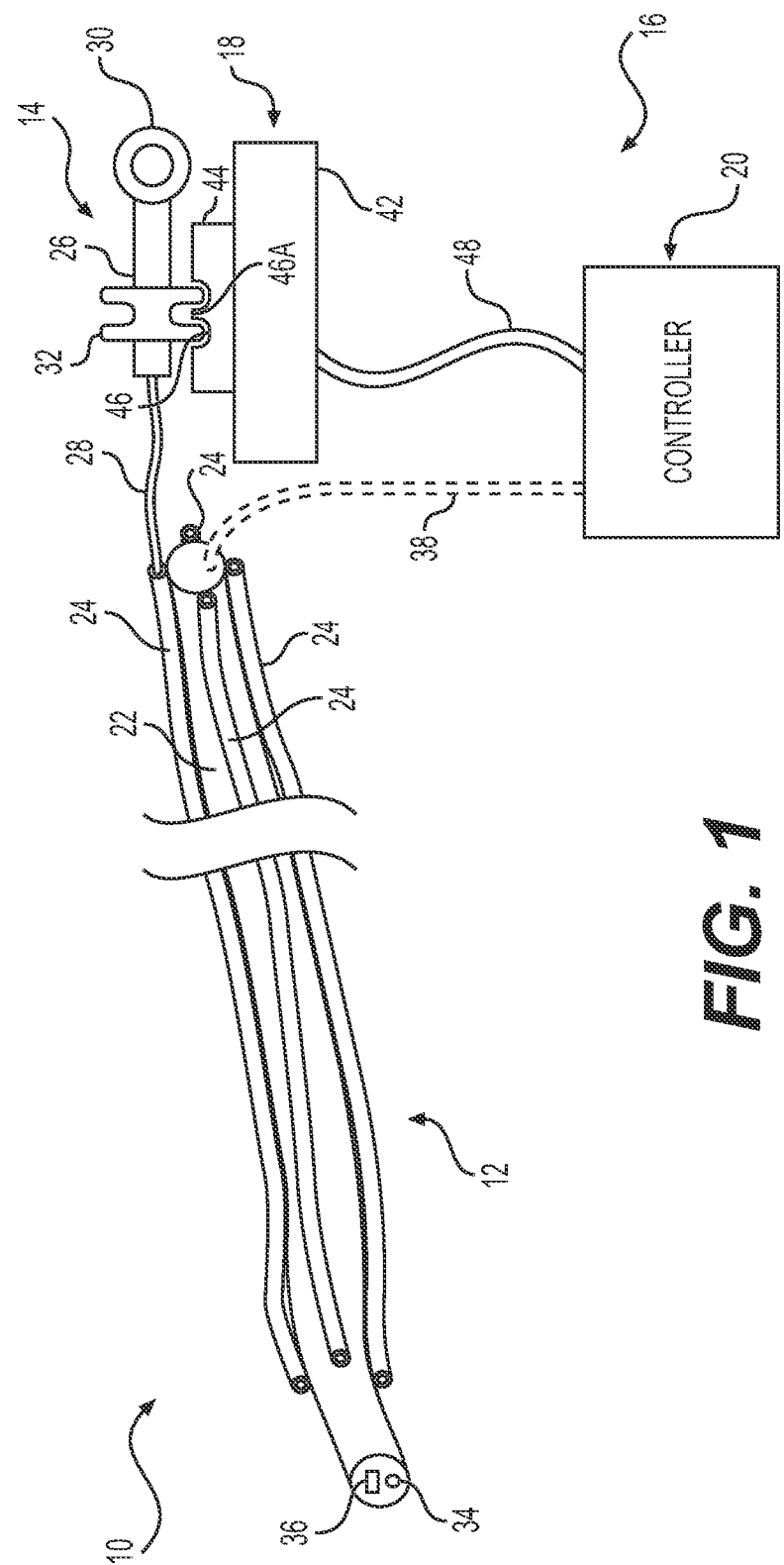
FIG. 1 illustrates an exemplary medical system, according to aspects of this disclosure.

The terms "proximal" and "distal" are used herein to refer to the relative positions of the components of an exemplary medical system and exemplary medical devices. When used herein, "proximal" refers to a position relatively closer to the exterior of the body or closer to a medical professional using the medical system or medical device. In contrast, "distal" refers to a position relatively further away from the medical professional using the medical system or medical device, or closer to the interior of the body. As used herein, the terms "comprises," "comprising," "having," "including," or other variations thereof, are intended to cover a non-exclusive inclusion, such that a system, device, or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Examples of the present disclosure include systems, devices, and methods for facilitating and/or improving the efficacy, efficiency, and/or safety of a medical procedure. Embodiments of the present disclosure may relate to systems, devices, and methods for performing various medical procedures and/or visualizing portions of the large intestine (colon), small intestine, cecum, esophagus, any other portion of the gastrointestinal tract, and/or any other suitable patient anatomy. Various embodiments described herein include single-use or disposable medical devices. Some aspects of the present disclosure may be used in performing an endoscopic, arthroscopic, or other type of procedure. For example, the disclosed aspects may be used with duodenoscopes, bronchoscopes, ureteroscopes, colonoscopes, catheters, diagnostic or therapeutic tools or devices, or other types of medical devices.

Embodiments of the present disclosure may be used to visualize, cut, resect, energize, treat, remove, couple, and/or manipulate target tissue in an endo-luminal space, or facilitate the process thereof. For example, aspects of the present disclosure may provide the user with the ability to deliver an insertion device to a location within a patient's body, and also to deliver a plurality of medical devices through lumens of the insertion device to the location within the patient's body to, for example, visualize, cut, resect, energize, treat, remove, couple, or otherwise manipulate tissue or material within a patient's body. Aspects of the present disclosure may provide a user (e.g., physician, medical technician, or other medical service provider) with the ability to deliver one or more medical devices with the assistance of an insertion device or delivery scope, and to direct the one or more medical devices in a different direction toward the treatment site than the insertion device or delivery scope. Additionally, aspects of the present disclosure may provide the user with the ability to separately control the position, direction, movement, and/or actuation of the one or more medical devices. The one or more medical devices may include, for example, one or more of a clip, a snare, a grasper, a camera, an illumination device, a needle, a knife, scissors, forceps, an electrosurgical tool (e.g., an Endoscopic Submucosal Dissection knife), etc. One or more of the elements discussed herein could be metallic, plastic, or include a shape memory metal (such as nitinol), a shape memory polymer, a polymer, or any combination of biocompatible materials.

Reference will now be made in detail to examples of the present disclosure described above and illustrated in the accompanying drawings. Wherever possible, the same reference numbers will be used throughout the drawings to refer to the same or like parts.

Figure 2A:
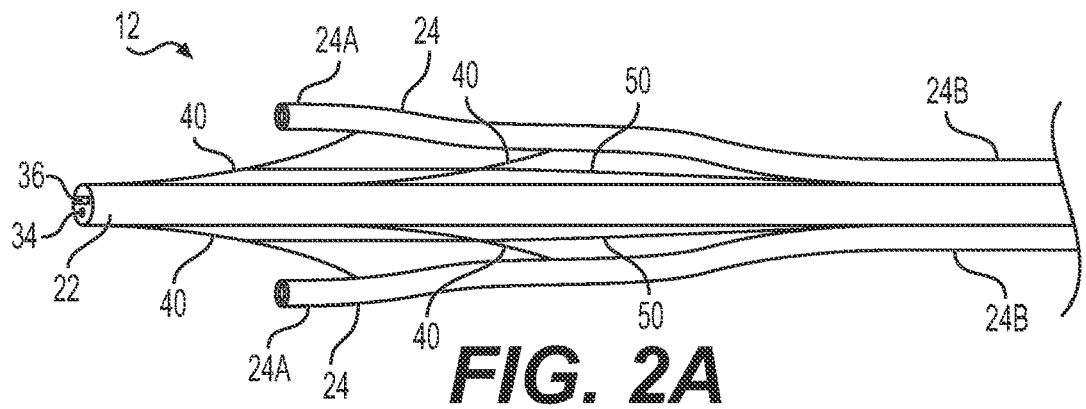
FIGS. 2A and 2B illustrate different views of a portion of the medical system in a collapsed configuration.
Figure 2B:
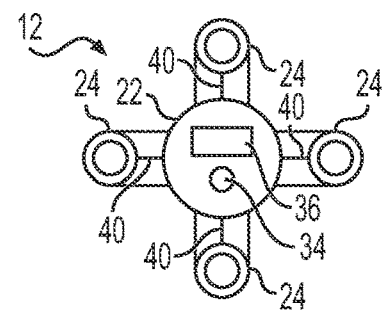
Figure 2C:
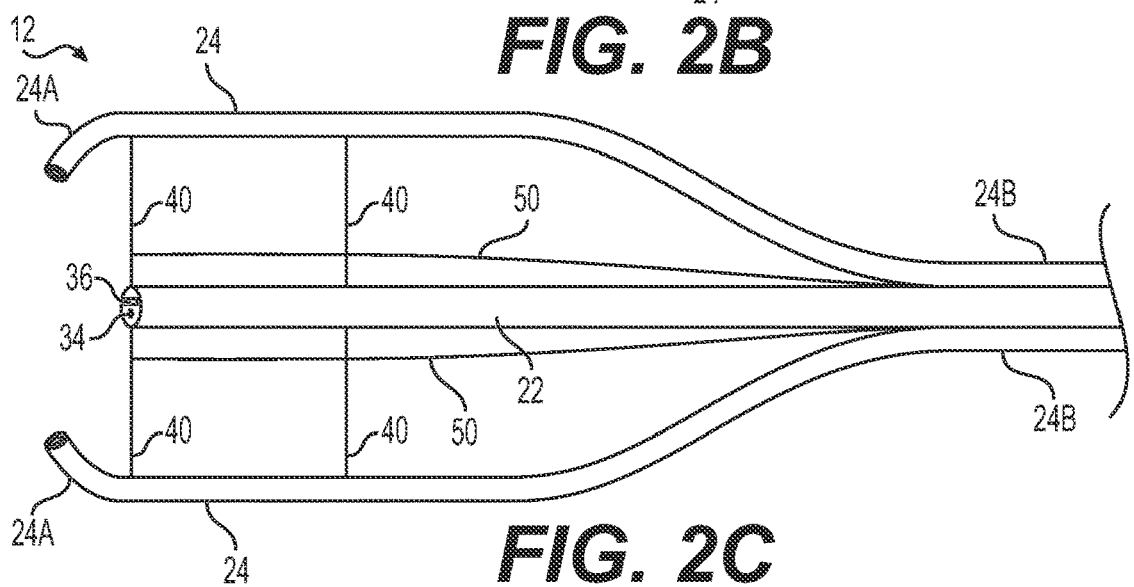
FIGS. 2C and 2D illustrate different views of the portion of the medical system in an expanded configuration, according to aspects of the present disclosure.

FIG. 1 depicts a medical system 10 that includes a platform device 12 and one or more medical devices 14. Medical system 10 may also include a control system 16, which includes an adaptor 18 and a controller 20. Platform device 12 includes a central or inner tube 22 and a plurality of outer tubes 24. Outer tubes 24 are positioned around the periphery of inner tube 22 and include central lumens. As shown in FIGS. 2A and 2C, outer tubes 24 are movably coupled to inner tube 22. As shown in FIG. 1, medical device 14 may include a handle 26 and an insertion portion 28. Handle 26 may include a stationary portion 30 and a movable portion 32, with the movable portion 32 controlling the movement and/or actuation of insertion portion 28. In the embodiment shown in FIG. 1, stationary portion 30 includes a thumb ring at a proximal end, and movable portion 32 is a spool that rides on stationary portion 30. Insertion portion 28 may include an end effector (not shown) at a distal end, and the movement and/or actuation of the end effector may be controlled by the movement of movable portion 32 of handle 26. Adaptor 18 and/or controller 20 may control a portion of handle 26, for example, movable portion 32, to control the movement and/or actuation of insertion portion 28 and the end effector.

It is noted that FIG. 1 is not to scale, and that platform device 12 is shown larger than the other components of medical system 10 in order to depict the various aspects of this disclosure.

As shown in FIG. 1, inner tube 22 may have a larger cross-sectional circumference, or diameter, than each of outer tubes 24. Inner tube 22 may also include one or more lumens 34 (for, e.g., irrigation, aspiration, and/or working tools) and/or a visualization device 36 (e.g., a camera and/or an illumination device). Optionally, inner tube 22 may also be coupled to control system 16 (e.g., to controller 20) via one or more cables 38. Outer tubes 24 may be coupled to inner tube 22. Although FIGS. 1 and 2A-2D show four outer tubes 24, this disclosure is not so limited. For example, platform device 12 may include one, two, three, five, six, etc. outer tubes 24. Outer tubes 24 may be evenly spaced around an outer circumference of inner tube 22. For example, as shown, with four outer tubes 24, outer tubes 24 may be positioned approximately ninety degrees apart along the outer circumference of inner tube 22. Alternatively, outer tubes 24 may be unevenly spaced around the outer circumference of inner tube 22.

Figure 2D:
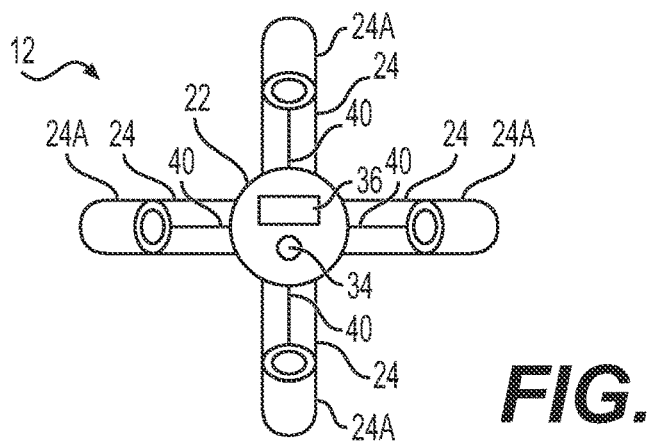

Outer tubes 24 may be coupled to inner tube 22 via a collapsible and expandable structure, or an "umbrella"-like structure, which allows for outer tubes 24 to be movable between a collapsed configuration (FIGS. 2A and 2B) and an expanded configuration (FIGS. 2C and 2D). FIGS. 2A and 2C are side views of platform device 12 with a front outer tube 24 and a rear outer tube 24 omitted for clarity, and FIGS. 2B and 2D are distal end views of platform device 12. It is noted, however, that FIGS. 2A and 2B illustrate outer tubes 24 being slightly spaced away from inner tube 22 in order to show supports 40 coupling outer tubes 24 to inner tube 22. Nevertheless, in the collapsed structure, outer tubes 24 may abut, or otherwise lie against or flush with, inner tube 22 along the entire longitudinal length of outer tubes 24, as shown in FIG. 1.

As shown in FIGS. 2A-2D, outer tubes 24 may be coupled to inner tube 22 via one or more supports 40, with supports 40 being movable to transition outer tubes 24 from the collapsed configuration to the expanded configuration, and vice versa. For example, each outer tube 24 may be coupled to inner tube 22 via two supports 40 positioned near distal portions 24A, as shown. Alternatively, each outer tube 24 may be coupled to inner tube 22 via a single support 40 or three or more supports 40. Supports 40 may be metallic, plastic, or include a shape memory metal (such as nitinol), a shape memory polymer, a polymer, or any combination of biocompatible materials. Supports 40 may be flexible, rigid, outwardly biased toward the expanded configuration, etc.

Additionally, in some aspects, one or more supports 40 may be coupled to one or more control wires 50. Control wire(s) 50 may be formed of the same material as supports 40, or may be formed of a different material, for example, a more rigid material. For example, each support 40 may be coupled to one control wire 50, or supports 40 for respective outer tubes 24 may be coupled to one control wire 50. In these aspects, control wires 50 may extend from supports 40 to a position proximal of platform device 12 (e.g., to a secondary movable portion on handle 26, to a secondary slider on adaptor 18, to controller 20, etc.), and may be controllable by a user and/or by control system 16. For example, control wires 50 may be retracted proximally to pull supports 40 proximally and draw outer tubes 24 toward inner tube 22. Similarly, control wire 50 may be extended distally to extend supports 40 distally and push outer tubes 24 away from inner tube 22.

Furthermore, as shown in FIG. 2C, when outer tubes 24 are in the expanded configuration, distal portion 24A of each outer tube 24 may be bent or curved radially inward, for example, toward a longitudinal axis of inner tube 22. For example, distal portions 24A may be formed of a shape-memory material. In one aspect, distal portions 24A of outer tubes 24 may be bent or curved radially inward at an angle of approximately 30-45 degrees, approximately 15-75 degrees, or up to approximately 180 degrees. Proximal portions 24B of outer tubes 24, however, may be straight and extend along (e.g., abut) inner tube 22. Although not shown, distal portions 24A of one or more outer tubes 24 may point straight or be bent or curved radially outward relative to the longitudinal axis of inner tube 22.

One or more outer tubes 24 may be larger or smaller than the other of the outer tubes 24, for example, to receive different sized medical devices 14 or to deliver different amounts of irrigation, suction, etc. Moreover, one or more medical devices 14 and outer tubes 24 may be separately articulated, for example, expandable to different radial distances from inner tube 22 in the expanded configuration and/or individually movable relative to inner tube 22 (e.g., by movement of separate control wires 50). Although not shown, one or more outer tubes 24 may extend proximally beyond inner tube 22, for example, in order to receive medical devices 14 and/or to be coupled to control system 16 (e.g., a robotically operated control system).

In one aspect, outer tubes 24 may be labeled and/or color coded. For example, both the proximal and distal ends may include an identifying label (e.g., numbering, lettering, etc.) and/or color. In some embodiments, each outer tube 24 has a different label or color. As such, a user viewing the treatment site and the distal portions 24A of outer tubes 24 (e.g., via visualization device 36) may distinguish between outer tubes 24, and may deliver medical device 14 through the proximal end of the appropriate outer tube 24 and/or manipulate or actuate a medical device 14 within the appropriate outer tube 24.

Platform device 12 may be coupled to and/or inserted through an insertion device to be delivered to a treatment site. In one aspect, platform device 12 may be inserted through an insertion sheath. In another aspect, platform device 12 may be coupled to any scope, for example, an endoscope (e.g., SpyGlass™ DS Direct Visualization by Boston Scientific Corp.), a hysteroscope, a bronchoscope, a cystoscope, or any similar endoscope device to be delivered to the treatment site. The endoscope may be placed in inner tube 22. Although inner tube 22 is shown as being generally cylindrical with one or more lumens, this disclosure is not so limited. For example, inner tube 22 may be any shape and may or may not include one or more lumens. Additionally, in yet further examples, inner tube 22 may itself be an endoscope, another type of scope with controllable articulation, visualization, one or more channels or lumens, etc., or any other insertion device (e.g., any device for inserting in a body and capable of being coupled to a platform device).

Medical device(s) 14 may be delivered through one or more outer tubes 24. Medical device(s) 14 may include a clip, a snare, a grasper, a camera, an illumination device, a needle, a knife, scissors, forceps, an electrosurgical tool (e.g., an Endoscopic Submucosal Dissection knife), etc. For example, one grasper, one forceps, one camera, and one illumination device may be delivered through respective outer tubes 24. Alternatively, one or more outer tubes 24 may be free of medical devices 14, and may be proximally sealed to help prevent fluid and/or air flow. Moreover, in another aspect, one or more outer tubes 24 may be free of medical devices 14, and may be coupled to an irrigation and/or suction source. In any of these aspects, a user may select which outer tube(s) 24 in which to position medical device(s) 14. For example, one outer tube 24 may provide an appropriate angle and/or position for a forceps to treat the treatment site, and another outer tube 24 may provide an appropriate angle and/or position for an illumination device. Additionally, medical devices 14 in different outer tubes 24 may be separately positioned, directed, moved, actuated, etc. without affecting a position, direction, movement, actuation, etc. of other medical devices 14 or inner tube 22.

Medical device(s) 14 may be controlled via control system 16 such that adaptor 18 and controller 20 may control the extension, retraction, rotation, actuation, etc. of the one or more medical devices 14. For example, as shown in FIG. 1, handle 26 of medical device 14 may be positioned within a portion of adaptor 18. Adaptor 18 may include a base 42 and a slider 44 that is movable relative to base 42. The movement of slider 44 may be controlled by controller 20. Accordingly, movable portion 32 of handle 26 may be positioned within a receiving portion 46 of slider 44 (e.g., a protrusion 46A of receiving portion 46 may be received in the spool of movable portion 32), and controller 20 may control the position and/or movement of slider 44 to control the position, direction, movement, and/or actuation of the end effector at the distal end of insertion portion 28. For example, controller 20 may be coupled to adaptor 18 via a cable 48.

Controller 20 may be a capital box (e.g., capital equipment) with one or more of a user interface, display, etc. Controller 20 may include stored instructions and/or receive user inputs for performing a medical procedure. Controller 20 may transmit signals to adaptor 18, e.g., via cable 48, in order to move slider 44 relative to base 42, and thus move movable portion 32 relative to stationary portion 30 to control the position, movement, direction, actuation, etc. of medical device 14. Additionally, controller 20 may receive and/or transmit information and signals to and from medical devices 14 and inner tube 22, either wirelessly or through a wired connection (e.g., via cable 38).

Although only one medical device 14 is shown in FIG. 1, this disclosure is not so limited. For example, medical devices 14 may be positioned within each outer tube 24 in order to perform a medical treatment. Alternatively, medical devices 14 may be positioned within any subset of outer tubes 24 in order to perform a medical treatment. Correspondingly, there may be multiple adaptors 18 to control multiple medical devices 14. Moreover, although not shown, medical devices 14 may include a drive wire coupled to the end effector and the movable portion 32, with the drive wire and the end effector being surrounded by and, optionally, movable relative to, a medical device sheath. As discussed below with respect to FIGS. 3 and 4, control system 16 may control the position, direction, movement, and/or actuation of a plurality of medical devices 14.

Figure 3:
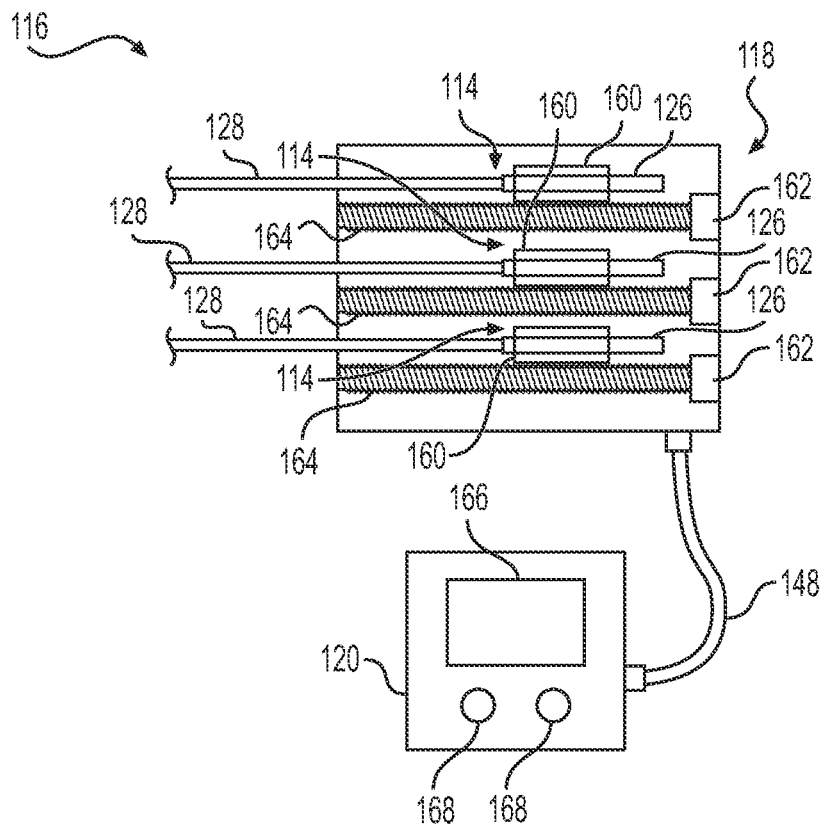
FIG. 3 illustrates an alternative configuration of a portion of the exemplary medical system of FIG. 1, according to aspects of the present disclosure.
Figure 4:
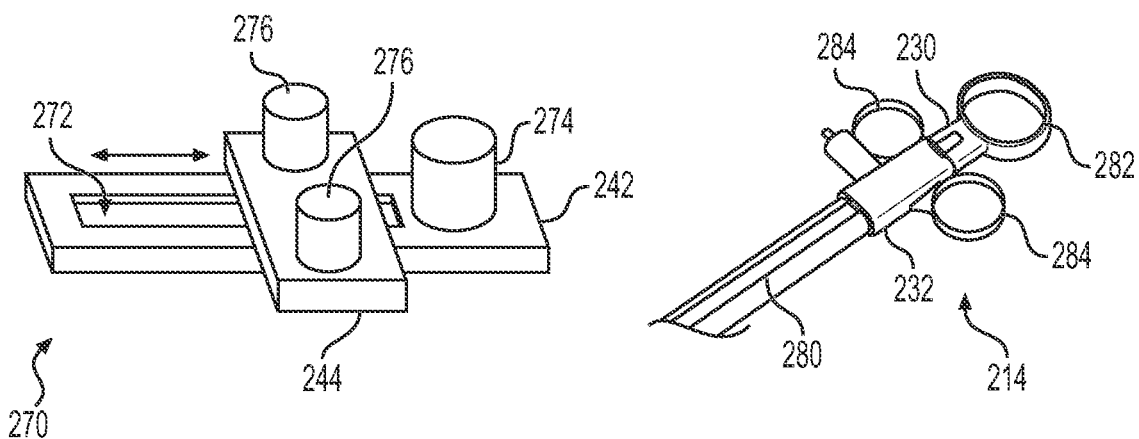
FIG. 4 illustrates another alternative configuration of another portion of the exemplary medical system of FIG. 1, according to aspects of the present disclosure.

FIGS. 3 and 4 illustrate alternative examples according to the present disclosure. FIG. 3 illustrates similar elements to medical system 10 shown by 100 added to the reference numbers. As shown in FIG. 3, a control system 116 may include an adaptor 118 and a controller 120.

Adaptor 118 may control the position, direction, movement, and/or actuation of a plurality of medical devices 114. For example, adaptor 118 may include a plurality of actuators 160, motors 162, and rotatable members or screws 164. Actuators 160 may be configured to be coupled to one or more medical devices 114, for example, to one or more handles 126, and control the activation of the insertion portions 128. Actuators 160 may include switches, solenoids, or other appropriate control devices to interact with and control the coupled medical device 114. For example, actuators 160 may control the extension of an end effector, the delivery of cautery energy through a cautery snare loop, the expansion of a retrieval basket, the illumination or image capture of an illumination or visualization device, the delivery or application of irrigation or suction, or other aspects of insertion portions 128. Actuators 160 may be separately controlled, and thus, medical devices 114 may be individually controlled.

Motors 162 may be configured to rotate screws 164, and medical devices 114 may be mounted screws 164. As such, rotation of screws 164 may rotate medical devices 114 and/or insertion portions 128. Motors 162 may be separately controlled to separately rotate screws 164, and thus, medical devices 114, and thus insertion portions 128, may be individually rotated. Alternatively, screws 164 may be used to translate medical devices 114.

Controller 120 is coupled to adaptor 118 via cable 148. Controller 120 may control actuators 160 and/or motors 162 to control the position, direction, movement, and activation of a plurality of medical devices 114, as discussed above. Additionally, controller 120 may include a user interface 166 (e.g., a touch screen display) and one or more input devices 168, for example, knobs, levers, joysticks, buttons, etc. to input or modify operating instructions to controller 120. Accordingly, controller 120 may execute or receive instructions and control a plurality of medical devices 114 to perform a procedure.

FIG. 4 illustrates an exemplary coupling mechanism 270 that may be incorporated on adaptor 18, 118 to couple a medical device 214, with similar elements to medical system 10 shown by 200 added to the reference numbers. Coupling mechanism 270 may include a base 242 and a slider 244. Base 242 includes a track 272 in which slider 244 may move. Base 242 also includes a base knob 274, and slider 244 may include two slider knobs 276.

As shown, medical device 214 may include a handle 226 with a stationary portion or a main body 230 and a movable portion or a movable body 232. In one aspect, movement of movable body 232 relative to main body 230 controls an extension or retraction of an end effector of medical device 214. Main body 230 may include a slot 280 and an opening 282 (e.g., to receive a user's thumb). Movable body 232 may be slidably positioned within slot 280 and include one or more holes 284 (e.g., to receive the user's fingers). In order to couple medical device 214 to coupling mechanism 270, base knob 274 may be positioned within opening 282, and slider knobs 276 may be positioned within holes 284. Alternatively, medical device 214 may be coupled to coupling mechanism 270 via clamps, pins, grooves, etc. Coupling mechanism 270 may be coupled to or otherwise be a part of adaptors 18, 118. Controllers 20, 120 may control the movement of slider 244 to control the movement of movable body 232, thus controlling the extension or retraction of an end effector of medical device 214 without the user having to hold medical device 214. Additionally, in one aspect, a plurality of coupling mechanisms 270 may be coupled to adaptors 18, 118, which may allow for controllers 20, 120 to control a plurality of medical devices 214. Each coupling mechanism 270 may be coupled to a different medical device 214.

Figure 5:
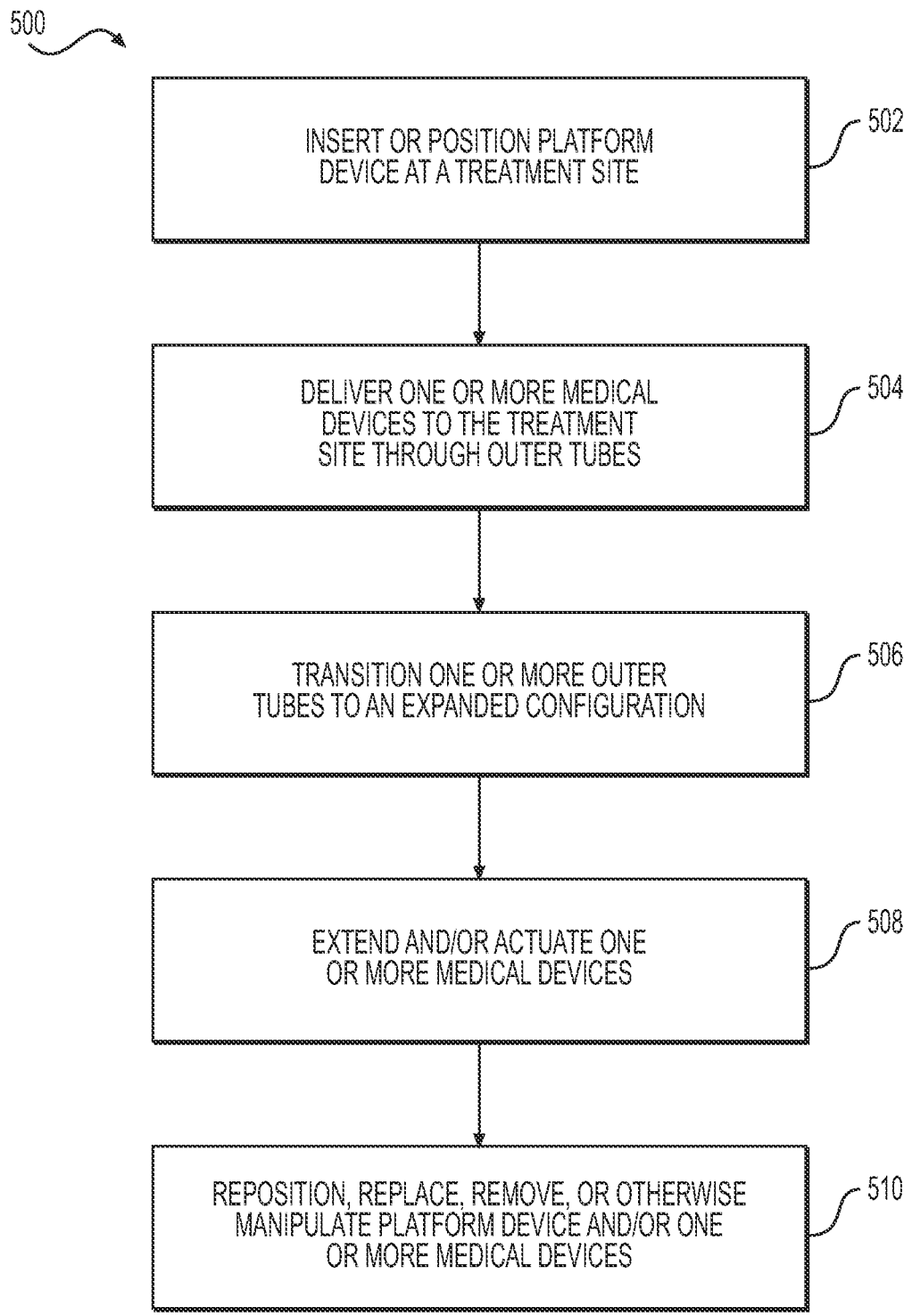
FIG. 5 is a flow diagram of an exemplary treatment method, according to aspects of the present disclosure.

FIG. 5 is a flow diagram portraying an exemplary treatment method 500 to treat, diagnose, and/or visualize a body lumen of a patient. Method 500 includes a step 502, in which platform device 12 is inserted or positioned at a treatment site, for example, within a large intestine of the patient. For example, step 502 may include coupling platform device 12 to a guide wire in order to insert or position platform device 12. Alternatively or additionally, platform device 12 may be delivered via an insertion device, for example, a scope, or through an insertion sheath. Alternatively or additionally, platform device 12 may be delivered over an insertion device, for example, an endoscope placed within inner tube 22. Once platform device 12 is positioned at the treatment site, the insertion device or sheath may be left in place, removed, or proximally retracted.

In a step 504, one or more medical devices 14 may be delivered to the treatment site through one or more outer tubes 24. For example, one medical device 14 may be delivered via any one of outer tubes 24, with the selected outer tube 24 corresponding to a position from which medical device 14 may extend and/or otherwise treat the treatment site. In another example, one medical device 14 (e.g., a forceps) may be delivered through a first outer tube 24, and another medical device 14 (e.g., an energy delivery device) may be delivered through a second outer tube 24, with the second outer tube 24 being adjacent to, opposite from, or otherwise positioned relative to the first outer tube 24 in order for the medical devices 14 to treat the treatment site effectively and/or efficiently.

In a step 506, which may be performed after step 504 or before step 504, one or more outer tubes 24 may be manipulated to transition from the collapsed configuration (FIG. 2A) to the expanded configuration (FIG. 2C). The transition may be effected by, for example, actuating or moving one or more control wires 50, as discussed above. For example, control wire(s) 50 may be controllable from a position proximal to platform device 12 to extend one or more outer tubes 24 either radially outward from inner tube 22 (relative to a longitudinal axis of inner tube 22) and/or distally beyond a distal face of inner tube 22. Alternatively or additionally, an outer sheath may be positioned around delivery platform 12, and one or more outer tubes 24 may be coupled to inner tube 22 via one or more biasing members. The one or more biasing members may be separate from or incorporated within supports 40. In this aspect, when the outer sheath is retracted proximally, an exposed portion of outer tubes 24 may expand outward due to the outward biasing force from the one or more biasing members.

In another aspect, one or more outer tubes 24 may transition from the collapsed configuration to the expanded configuration via an umbrella mechanism. For example, one or more supports 40 may include one or more hinges where the one or more supports 40 contact outer tubes 24 and inner tube 22. Pushing control wire(s) 50 distally may cause the hinges to turn, thus pushing outer tubes 24 radially outward, or away from inner tube 22. Additionally or alternatively, one or more supports 40 may include hinges where the one or more supports 40 are connected to control wire(s) 50 such that pushing control wire(s) 50 causes the hinges to turn, thus pushing outer tubes 24 radially outward. Moreover, the transition from the collapsed configuration to the expanded configuration may be controlled via controller 20, 120, for example, by controller 20, 120 signaling or otherwise controlling the movement of control wire(s) 50, the outer sheath, etc.

In a step 508, one or more medical devices 14 positioned within one or more outer tubes 24 may be distally extended or otherwise actuated to treat the treatment site. For example, handles 26, 126, 226 coupled to medical devices 14, 114, 214 may be manually controlled to extend or otherwise actuate medical devices 14, 114, 214. Alternatively, as discussed with above, adaptors 18, 118, 218 and controllers 20, 120 may control the position, direction, movement, and/or actuation of one or more medical devices 14, 114, 214.

Next, in a step 510, platform device 12 and/or one or more medical devices 14, 114, 214 may be repositioned, replaced, removed, or otherwise manipulated. For example, one medical device 14, 114, 214 may be repositioned with respect to the treatment site, for example, by further extending medical device 14, 114, 214 from outer tube 24, by removing medical device 14, 114, 214 from a first outer tube 24 and inserting medical device 14, 114, 214 into a second outer tube 24 that provides a different position and/or angle and direction of approach relative to the treatment site, by repositioning platform device 12 itself, etc. Medical device 14, 114, 214 may be removed from outer tube 24, and replaced with another medical device 14, 114, 214. For example, scissors may be used to cut tissue at the treatment site. The scissors may be removed from outer tube 24, and then a grasper may be delivered through outer tube 24 to capture the cut tissue. Medical device 14, 114, 214 may be removed entirely from outer tube 24. For example, a retrieval basket may be used to capture material at the treatment site, and the retrieval basket may be removed from outer tube 24 to remove the captured material from the patient. Moreover, the position of inner tube 22, one or more outer tubes 24, medical device 14, 114, 214 or other components of system 10 may be manipulated to perform the medical procedure, either manually by the user or via controller 20, 120.

Lastly, although not shown in method 500, a user may remove platform device 12 and any medical devices 14, 114, 214 within outer tubes 24 from the patient.

The aforementioned aspects may allow platform device 12 to be delivered to a treatment site. A user may position platform device 12 relative to the treatment site (e.g., via visualization on a delivery scope or through visualization device 36 on inner tube 22) and transition outer tubes 24 from the collapsed configuration to the expanded configuration. The outer tubes 24 may provide a number of positions and/or angles relative to the treatment site. One or more medical devices 14, 114, 214 may be selectively delivered through outer tubes 24 and positioned and/or manipulated at different angles relative to the treatment site. Medical device(s) 14, 114, 214 may also be positioned, directed, moved, actuated, etc. without changing the position, direction, movement, or actuation of other medical devices 14, 114, 214, inner tube 22, or other aspects of system 10. As a result, the medical procedure may be quicker, more effective, more efficient, etc. because medical devices 14, 114, 214 may be able to "triangulate" the treatment site and treat the treatment site without having to reposition the medical devices as frequently compared to medical devices delivered through an access lumen of a scope.

Moreover, adaptors 18, 118 and coupling mechanism 270 may allow for handles 26, 126, 226 of a number of medical devices 14, 114, 214 to be quickly coupled, uncoupled, and otherwise controlled by control system 16. Control system 16 may allow for a greater number of medical devices 14, 114, 214 to be involved simultaneously in a medical procedure, without requiring the user(s) to hold and manually manipulate each medical device 14, 114, 214. Moreover, as discussed with respect to FIGS. 1 and 3, controllers 20, 120 may automatically control adaptors 18, 118 to control the position, direction, movement, and/or actuation of one or more medical devices 14, 114, 214, which may help the medical procedure be quicker, more effective, more efficient, etc.

Although the aspects of medical system 10 discussed above and method 500 are discussed as being used to treat a treatment site in a large intestine (colon), small intestine, cecum, or esophagus, these aspects and methods may be used to perform any medical procedure, and may help to reduce the overall procedure time, component costs, reduce the risks to the subject, etc.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical system comprising:
a plurality of tubes arranged about a periphery of an insertion device, a lumen of each of the plurality of tubes being configured to receive a medical device;
wherein each of the tubes is coupled to the periphery of the insertion device via one or more supports;
wherein the one or more supports are movable to transition one or more corresponding tubes from a collapsed configuration adjacent the periphery of the insertion device to an expanded configuration further radially outward of and spaced away from the periphery of the insertion device as compared to the collapsed configuration;
wherein each of the one or more supports is coupled to a respective independently movable control wire to move each of the one or more supports in a proximal direction or a distal direction; and
wherein the one or more control wires are configured to push the one or more corresponding tubes away from the periphery of the insertion device to the expanded configuration.

2. The medical system of claim 1, wherein movement of the one or more supports in the distal direction transitions the one or more corresponding tubes from the collapsed configuration to the expanded configuration.

3. The medical system of claim 2, wherein the one or more supports bias the tubes toward the expanded configuration.

4. The medical system of claim 2, wherein, in the expanded configuration, a distal portion of at least one tube is curved or bent radially inward toward a longitudinal axis of the insertion device.

5. The medical system of claim 2, wherein movement of the one or more control wires in the distal direction transitions the one or more corresponding tubes from the collapsed configuration to the expanded configuration.

6. The medical system of claim 2, wherein, in the expanded configuration, proximal portions of the tubes contact the insertion device.

7. The medical system of claim 2, further including a control system, including an adaptor and a controller, wherein the adaptor is configured to receive a portion of the medical device.

8. The medical system of claim 7, wherein the adaptor includes a base and a slider that is movable relative to the base, and wherein the slider includes a receiving portion configured to receive the portion of the medical device.

9. The medical system of claim 8, wherein the controller is coupled to the adaptor, and wherein the controller automatically controls the movement of the slider relative to the base.

10. The medical system of claim 9, wherein the controller is coupled to the insertion device to automatically control one or more operations of the insertion device.

11. The medical system of claim 7, wherein the adaptor includes a plurality of actuators, a plurality of motors, and a plurality of rotatable members coupled to the motors.

12. The medical system of claim 11, wherein each actuator of the plurality of actuators is configured to be coupled to a handle of a corresponding medical device, and
wherein the plurality of motors and the plurality of rotatable members are configured to rotate and/or translate the medical device when the medical device is coupled to the corresponding actuator of the plurality of actuators.

13. The medical system of claim 7, wherein the adaptor includes a coupling mechanism with a base and a slider that is movable relative to the base and along a track of the base, wherein the base includes a base knob proximal of the track and configured to be coupled to a main body of a handle of the medical device, and wherein the slider includes two slider knobs configured to be coupled to a movable body of the handle of the medical device.

14. The medical system of claim 2, wherein the plurality of tubes includes two to six tubes, and wherein the tubes are approximately evenly spaced around the periphery of the insertion device.

15. The medical system of claim 2, wherein the insertion device includes a visualization device positioned at a distal end of the insertion device.

16. A medical system comprising:
a platform device including an inner tube and a plurality of outer tubes arranged about a periphery of the inner tube, wherein each of the outer tubes is coupled to a distal portion of the inner tube via one or more movable supports, wherein the one or more movable supports are configured to push a distal portion of a corresponding outer tube radially away from a longitudinal axis of the inner tube such that the distal portion of the corresponding outer tube is spaced away from the periphery of the inner tube, wherein each of the movable supports is coupled to one or more control wires to move each of the movable supports proximally or distally relative to the inner tube, wherein each of the outer tubes is configured to receive a medical device, and wherein each of the outer tubes is separately movable;

an adaptor configured to receive a portion of the medical device, wherein the adaptor includes a base and a slider configured to move relative to the base, and wherein the slider includes two knobs configured to be coupled to a movable body of the medical device; and a controller configured to automatically control movement of the medical device relative to a corresponding outer tube of the plurality of outer tubes.

17. The medical system of claim 16, wherein, in a configuration in which the distal portion of at least one outer tube is radially away from the longitudinal axis of the inner tube, the distal portion of the at least one outer tube is curved or bent radially inward toward the longitudinal axis of the inner tube, and a proximal portion of the at least one outer tube contacts the inner tube.

18. The medical system of claim 16, wherein the adaptor further includes at least one actuator configured to be coupled to a handle of the medical device, a motor, and a rotatable member coupled to the motor, wherein the controller is coupled to the adaptor and controls the movement of the at least one actuator, the motor, the rotatable member, and the slider, wherein the base includes a base knob, and wherein the base knob is positioned on the base proximal of the slider.

19. A method, comprising:

positioning a platform device at a treatment site, wherein the platform device includes an inner tube and a plurality of outer tubes arranged about a periphery of the inner tube, wherein each of the outer tubes is coupled to the periphery of the inner tube via one or more movable supports, wherein each of the movable supports is coupled to one or more separate control wires, and wherein the one or more separate control wires extend from a portion of the movable supports to a proximal portion of the platform device;

coupling one or more medical devices to an adaptor, wherein the adaptor is configured to receive a handle of the one or more medical devices, and wherein the adaptor includes a base and a slider configured to move relative to the base, and wherein the slider includes two knobs configured to be coupled to a movable body of the handle of the one or more medical devices;

delivering the one or more medical devices to the treatment site through one or more of the outer tubes;

transitioning one or more of the outer tubes to an expanded configuration in which a distal portion of the one or more outer tubes is further radially away from the periphery of the inner tube; wherein transitioning one or more of the outer tubes to the expanded configuration includes separately pushing one or more of the control wires distally to separately extend each of the one or more movable supports distally, and wherein extending each of the one or more movable supports distally pushes the distal portion of one or more corresponding outer tubes away from the periphery of the inner tube to the expanded configuration; and extending or actuating the one or more medical devices.

20. The method of claim 19, further comprising repositioning, replacing, removing, or manipulating the platform device or the one or more medical devices.

* * * * *